United States Patent
Berrebi-Bertrand et al.

(10) Patent No.: US 9,242,959 B2
(45) Date of Patent: Jan. 26, 2016

(54) (AZA)BENZHYDRYL ETHER DERIVATIVES, THEIR PROCESS OF PREPARATION AND THEIR USE AS H4-RECEPTOR LIGANDS FOR THERAPEUTICAL APPLICATIONS

(71) Applicant: BIOPROJET, Paris (FR)

(72) Inventors: Isabelle Berrebi-Bertrand, Pace (FR); Xavier Billot, Rennes (FR); Thierry Calmels, Melesse (FR); Marc Capet, Melesse (FR); Stéphane Krief, Rennes (FR); Olivier Labeeuw, Fougeres (FR); Jeanne-Marie Lecomte, Paris (FR); Nicolas Levoin, L'Hermitage (FR); Xavier Ligneau, Saint Gregoire (FR); Philippe Robert, Pace (FR); Jean-Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 0 days.

(21) Appl. No.: 13/910,651

(22) Filed: Jun. 5, 2013

(65) Prior Publication Data

US 2013/0324507 A1 Dec. 5, 2013

(30) Foreign Application Priority Data

Jun. 5, 2012 (EP) .................... 12305632

(51) Int. Cl.
*A61K 31/4545* (2006.01)
*A61K 31/445* (2006.01)
*A61K 45/06* (2006.01)
*C07D 401/12* (2006.01)
*C07D 211/22* (2006.01)
*C07D 211/46* (2006.01)

(52) U.S. Cl.
CPC .......... *C07D 401/12* (2013.01); *A61K 31/445* (2013.01); *A61K 31/4545* (2013.01); *A61K 45/06* (2013.01); *C07D 211/22* (2013.01); *C07D 211/46* (2013.01)

(58) Field of Classification Search
CPC . A61K 45/06; A61K 31/4545; A61K 31/445; C07D 401/12; C07D 211/22; C07D 211/46
USPC .......................................... 546/194; 514/318
See application file for complete search history.

(56) References Cited

U.S. PATENT DOCUMENTS

| 2,479,843 | A | * | 8/1949 | Howland et al. | 546/216 |
|---|---|---|---|---|---|
| 2,745,837 | A | * | 5/1956 | Papa et al. | 546/216 |
| 2,974,146 | A | * | 3/1961 | Biel | 546/216 |
| 3,280,196 | A | * | 10/1966 | Schilling | 568/661 |
| 4,874,765 | A | | 10/1989 | Lapis et al. | |
| 7,432,378 | B2 | | 10/2008 | Edwards et al. | |
| 7,662,966 | B2 | | 2/2010 | Edwards et al. | |
| 7,705,143 | B2 | | 4/2010 | Buzard et al. | |
| 7,705,149 | B2 | | 4/2010 | Edwards et al. | |
| 7,723,359 | B2 | | 5/2010 | Edwards et al. | |
| 7,723,526 | B2 | | 5/2010 | Edwards et al. | |
| 7,723,527 | B2 | | 5/2010 | Arienti et al. | |
| 2007/0173486 | A1 | * | 7/2007 | Davidson et al. | 514/210.01 |
| 2008/0207593 | A1 | * | 8/2008 | Heffernan et al. | 514/214.02 |
| 2009/0176792 | A1 | | 7/2009 | Gant et al. | |
| 2009/0247508 | A1 | | 10/2009 | Edwards et al. | |
| 2009/0270611 | A1 | | 10/2009 | Edwards et al. | |
| 2009/0281307 | A1 | | 11/2009 | Arienti et al. | |

FOREIGN PATENT DOCUMENTS

| DE | 934890 | * | 11/1955 |
|---|---|---|---|
| EP | 0243903 | * | 4/1987 |
| GB | 780027 | * | 7/1957 |
| KR | 2011036191 | * | 4/2011 |
| WO | WO9701340 | * | 1/1997 |
| WO | WO 2012/041860 | | 4/2012 |

OTHER PUBLICATIONS

Jilek; Collect. Czech. Chem. Commun., 1989, 54, 2248-2260.*
"Side Reactions in Organic Synthesis: A Guide to Successful Synthesis Design" 2005 Wiley-VCH Verlag GmbH & Co. KGaA, Wienheim, chapter 1.*
Lyseng-Williamson; Drugs, 2010, 70, 1579-1591.*
Physicians Desk Reference, label information for Advil Allergy Sinus, Jun. 2011.*
Iwasaki; Chemical and Pharmaceutical Bulletin, 1994, 42, 2276-2284.*
Lapa; Bioorganic and Medicinal Chemistry Letters, 2005, 15, 4915-4918.*
Weis; European Journal of Medicinal Chemistry, 2008, 43, 872-879.*
Wuts and Greene; "Green's protective groups in Organic Synthesis", 2007, 4th Ed, Wiley, pp. 803-806.*
European Search Report for EP 12 30 5632 dated Nov. 1, 2012.
Jilek J et al: "Potential Anticonvulsants: 3-Chlorobenzophenone Derivatives", Collection of Czechoslovak Chemical Communications, vol. 54, No. 8, (Jan. 1, 1989), pp. 2248-2260.
Database Registry Chemical Abstracts Service, Columbus, Ohio, US; Technical Fields Searched (MC) (Aug. 29, 2002), XP002686332, Database accession No. RN: 445394-44-5.
Database Registry Chemical Abstracts Service, Columbus, Ohio, US; (Aug. 29, 2002), XP002686333, Database accession No. RN: 445391-64-0.
Database Registry Chemical Abstracts Service, Columbus, Ohio, US; (Jun. 1, 2008), XP002686334, Database accession No. RN: 1024191-91-0.

* cited by examiner

*Primary Examiner* — Janet L Andres
*Assistant Examiner* — Daniel Carcanague
(74) *Attorney, Agent, or Firm* — B. Aaron Schulman, Esq.; Stites & Harbison, PLLC.

(57) ABSTRACT

The present invention concerns novel (aza)benzhydryl ether derivatives which exhibit H4-receptor binding activity. The present invention also concerns their process of preparation and their therapeutical uses.

14 Claims, No Drawings

(AZA)BENZHYDRYL ETHER DERIVATIVES, THEIR PROCESS OF PREPARATION AND THEIR USE AS H4-RECEPTOR LIGANDS FOR THERAPEUTICAL APPLICATIONS

The present patent application concerns novel (aza)benzhydryl ether derivatives as ligands of the H4-receptor, their process of preparation and their therapeutic use.

Until recently, the pro-inflammatory actions of histamine were thought to be essentially mediated by the H1 receptor and H1 receptor antagonists have found large therapeutic applications in allergic manifestations like the anaphylactic shock, allergic rhinitis, dermatitis, pruritus, etc.

However these drugs essentially prevent the occurrence of major symptoms of these manifestations without modifying clearly the progressive development of the inflammatory process leading to chronic diseases like asthma in which, however, histamine release from mast-cells might represent an important trigger (reviewed in Galli et al, Nature, 2008, 454, 445).

The recent discovery of the histamine H4 receptor (H4R) has modified this landscape (reviewed in Thurmond et al, Nature Rev. Drug Disc., 2008, 7, 41). The H4R belongs to the superfamily of G-protein coupled heptahelical receptors and is expressed on the plasma membranes of a variety of immunocompetent/inflammatory cells, e.g. eosinophils, basophils, mast-cells or dendritic cells. The H4R has a chimiotactic role, controlling the afflux of e.g. mast-cells or eosinophils to inflammatory sites that is elicited by histamine release and, thereby plays a major role in the development of chronic inflammatory disorders. It also controls the activity of eosinophils and some classes of lymphocytes. Blockade of the H4R by antagonists or inverse agonists should therefore constitute a novel therapeutic approach in diseases like asthma, emphysema, allergic rhinitis, nasal congestion, bronchitis, chronic obstructive pulmonary disease, dermatitis, arthritis, psoriasis, colitis, etc. in which they could be used alone or in association with already used other classes of anti-inflammatory medications, namely H1R antagonists. In addition the utilisation of H4R antagonists/inverse agonists is also of potential interest in a variety of autoimmune diseases e.g. type I diabetes, Crohn's disease, multiple sclerosis, lupus, etc. . . . The itch-preventing effect of some H4R antagonists in a rodent model (Bell et al, Br J Pharmacol, 2004, 142, 374) also suggests the use of these agents in pruritus, a manifestation only imperfectly controlled by available medications, namely H1R antagonists.

H4R antagonists/inverse agonists have not yet reached clinical uses and there is therefore a need for compounds displaying high potency and safety. In the present application a novel chemical class of H4R ligands is disclosed.

The instant invention thus relates to novel (aza)benzhydryl ether derivatives as H4 receptor ligands, to their preparation and to their application in therapeutics.

The present invention concerns new compounds of formula (I):

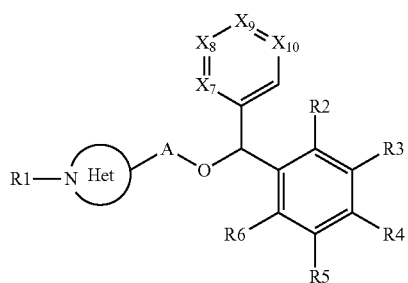

(I)

R1 represents a C1-C6 alkyl;

Het represents a non aromatic monocyclic 3 to 7 membered heterocycle containing one nitrogen atom and optionally 1 to 3 additional heteroatoms, wherein said at least one nitrogen atom is linked to R1;

A represents a single bond or a —C1-C6 alkyl-group;

Each R2, R3, R4, R5, R6 identical or different is independently chosen from:

hydrogen halo; azido; cyano; hydroxy; nitro;

alkyl; alkoxy; alkylsulfanyl; alkenyl; alkynyl; alkenyloxy; alkenyloxy; alkenylsulfanyl; alkynylsulfanyl; cycloalkoxy; cycloalkylalkyl;

whose alkyl, alkenyl, alkynyl or cycloalkyl part can be substituted with one or more of halo, hydroxy, polyhydroxy, alkoxy, hydroxyalkoxy, cyano, amino, aminoalkyl, alkylamino, dialkylamino, aminoalkylamino, aminoalkylaminocarbonyl, alkoxycarbonylamino, diarylmethylimino (where aryl is optionally substituted with one or more of hydroxy or halo), cycloalkenylimino (where cylalkenyl is optionally substituted with one or more of alkyl, OH), alkylsulfanyl, alkylsulfinyl, alkylsulfonyl, cycloalkyl, polycycloalkyl, cycloalkenyl, polycycloalkenyl, guanidino, alkylcarbonylguanidino, acylguanidino, cyanoguanidino, alkoxycarbonylguanidino, alkoxycarbonyl, alkoxycarbonylalkylamino, alkoxycarbonylalkylcycloalkyl, alkoxycarbonylheterocyclyl, aminocarbonyl, alkylaminocarbonyl, alkylcarbonyl, alkylcarbonylalkoxy, aryloxy, arylsulfanyl, arylsulfinyl, arylsulfonyl, heteroaryl, heterocyclyl (heterocyclyl being optionally substituted with one or more of oxo, amino, imino), heteroaryloxy, heterocyclyloxy, heteroarylamino, heterocyclylamino, hydrazinocarbonyl, hydroxyalkylcycloalkyl, N-alkyl(thioureido), phtalimido, ureido, oxocycloalkenylamino substituted with amino, carbamimidoylheterocyclyl;

amino; alkylamino; alkylcarbonyl; alkoxycarbonyl; alkylsulfanyl; alkylsulfinyl; alkylsulfonyl; alkylsulfonyloxy wherein:

alkyl can be substituted with one or more of halo;

and at least one of R2, R3, R4, R5, R6 is different from H each Xi, identical or different is chosen from —N═, —C(Ri)═ and —C(Ri')═, i representing the 7, 8, 9 or 10 indicia wherein either one of the Xi is —N═ and the others are —C(Ri)═ or either each Xi is chosen from —C(Ri)═ and —C(Ri')═ with at least one of Xi being —C(Ri')═ wherein for each i said Xi may be identical or different and said Ri may be identical or different so that

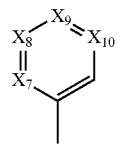

represents a substituted phenyl or an optionally substituted pyridyl, said Ri(i=7, 8, 9, 10) are chosen from
H
Ri'(i'=7, 8, 9, 10)
said Ri'(i'=7, 8, 9, 10) are chosen from:
halo, cyano, hydroxy, nitro,
alkyl; alkoxy; alkylsulfanyl; alkenyl; alkynyl; alkenyloxy; alkenyloxy; alkenylsulfanyl; alkynylsulfanyl; cycloalkoxy; cycloalkylalkyl
whose alkyl, alkenyl, alkynyl or cycloalkyl part can be substituted with one or more of halo, hydroxy, polyhydroxy, alkoxy;
aryl; arylalkyl; aryloxy; arylalkoxy; arylalkylamino; arylalkylsulfanyl; heteroaryl; heteroaryloxy
whose (hetero)aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro, cyanoalkyl, or fused with a non aromatic heterocycle;
and wherein R9 and R10 can form together with the C atoms to which they are attached an aromatic ring
as well as its enantiomers, diastereomers, mixtures thereof and pharmaceutically acceptable salts, tautomers, hydrates and solvates,
with the exception of the compounds where simultaneously:
X9 is —CR9'=,
X7=X8=X10=—CH=,
R4 is not H and
R2=R3=R5=R6=H.

According to an embodiment, X7, X8, X9, X10, R2, R3, R4, R5 and R6 are such as defined above, that the biaromatic moiety of the ether does not represent a benzhydryl substituted on its two para positions only.

According to an embodiment, the compounds of formula (I) are of formula (Ia):

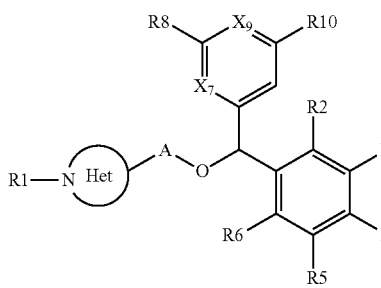

(Ia)

wherein
R1, Het, A, R2-6 are defined as in formula (I)
X7 or X9 represents —N= and the other of X7 or X9 represents —CR7= or —CR9=
And where R8, R10 and optional R7 or R9, identical or different are chosen from
H
halo, cyano, hydroxy, nitro,
alkyl; alkoxy; alkylsulfanyl; alkenyl; alkynyl; alkenyloxy; alkenyloxy; alkenylsulfanyl; alkynylsulfanyl; cycloalkoxy; cycloalkylalkyl
whose alkyl, alkenyl, alkynyl or cycloalkyl part can be substituted with one or more of halo, hydroxy, polyhydroxy, alkoxy;
aryl; arylalkyl; aryloxy; arylalkoxy; arylalkylamino; arylalkylsulfanyl; heteroaryl; heteroaryloxy
whose (hetero)aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro, cyanoalkyl, or fused with a non aromatic heterocycle;
and wherein R9 and R10 can form together with the C atoms to which they are attached an aromatic ring.

According to an alternative embodiment, the compounds of formula (I) are of formula (Ib):

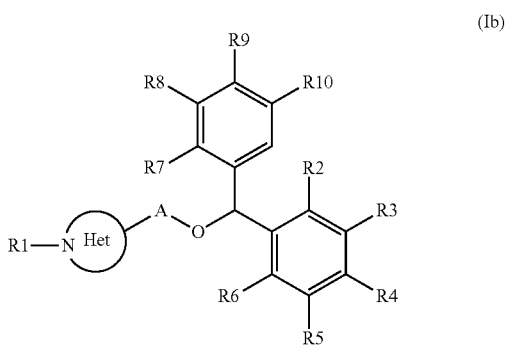

(Ib)

wherein:
R1, Het, A, R2-6 are defined as in formula (I) and
Each of R7-R10 is chosen from
H
halo, cyano, hydroxy, nitro,
alkyl; alkoxy; alkylsulfanyl; alkenyl; alkynyl; alkenyloxy; alkenyloxy; alkenylsulfanyl; alkynylsulfanyl; cycloalkoxy; cycloalkylalkyl
whose alkyl, alkenyl, alkynyl or cycloalkyl part can be substituted with one or more of halo, hydroxy, polyhydroxy, alkoxy;
aryl; arylalkyl; aryloxy; arylalkoxy; arylalkylamino; arylalkylsulfanyl; heteroaryl; heteroaryloxy
whose (hetero)aryl part can be substituted with one or more of amino, halo, alkyl, (poly)haloalkyl, hydroxyalkyl, alkoxy, (poly)haloalkoxy, alkoxycarbonylamino, alkylcarbonyl, alkylsulfanyl, alkylsulfinyl, alkylsulfonyl, nitro, cyanoalkyl, or fused with a non aromatic heterocycle;
and wherein R9 and R10 can form together with the C atoms to which they are attached an aromatic ring;
wherein at least of R7-R10 is different from H, and
with the proviso that
when R9 is not H, R7=R8=R10=H, and R2=R3=R5=R6=H, then R4 is H; or
when R4 is not H, R7=R8=R10=H, and R2=R3=R5=R6=H then R9 is H.

The compounds of formula (I), (Ia) and (Ib) of the invention also include the following particular embodiments or any of their combinations:
R1 represents a methyl; and/or
Het represents a piperidine; and/or
A represents a single bond; and/or
each R2, R3, R4, R5, R6 identical or different is independently chosen from:
hydrogen
halo; hydroxy;
alkyl; alkoxy; alkenyl;
whose alkyl, alkenyl, alkynyl part can be substituted with one or more of halo, amino, alkoxycarbonylamino, where at least one of R2, R3, R4, R5, R6 is different from H;
R2 and R5 are preferably H;

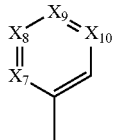

represents a substituted phenyl or an optionally substituted pyridyl,
said substituent(s) are chosen from
H
Ri'
said Ri' are chosen from:
halo, cyano,
alkyl optionally substituted with one or more of halo;
aryl;
and wherein R9 and R10 can form together with the C atoms to which they are attached an aromatic ring
with the exception of the compounds where simultaneously:
X9 is —CR9'=,
X7=X8=X10=—CH=,
R4 is not H and
R2=R3=R5=R6=H.
According to a further embodiments the compounds of the invention may be chosen from:
2-[(2-Fluoro-5-trifluoromethoxyphenyl)(1-methylpiperidin-4-yloxy)methyl]pyridine
5-Chloro-2-[(2-fluoro-4-methylphenyl)(1-methylpiperidin-4-yloxy)methyl]pyridine
2-[(2-Fluoro-4-methylphenyl)(1-methylpiperidin-4-yloxy)methyl]pyridine
5-Chloro-2-[(2-fluoro-5-trifluoromethoxyphenyl)(1-methylpiperidin-4-yloxy)methyl]pyridine
6-{3-[(1-Methylpiperidin-4-yloxy)pyridin-2-ylmethyl]phenyl}hex-5-ynylamine
4-[(2-Fluoro-5-trifluoromethoxyphenyl)(1-methylpiperidin-4-yloxy)methyl]pyridine
2-[(2-Fluoro-4-methylphenyl)(1-methylpiperidin-4-yloxy)methyl]-4-methylpyridine
2-[(2-Fluoro-5-trifluoromethoxyphenyl)(1-methylpiperidin-4-yloxy)methyl]-4-methylpyridine
5-Chloro-2-[(4-chlorophenyl)(1-methylpiperidin-4-yloxy)methyl]pyridine
5-Fluoro-2-[(2-fluoro-4-methylphenyl)(1-methylpiperidin-4-yloxy)methyl]pyridine
5-Fluoro-2-[(2-fluoro-5-trifluoromethoxyphenyl)(1-methylpiperidin-4-yloxy)methyl]pyridine
5-Chloro-2-[(3-methoxyphenyl)(1-methylpiperidin-4-yloxy)methyl]pyridine
5-Chloro-2-[(3-iodophenyl)(1-methylpiperidin-4-yloxy)methyl]pyridine
2-[(2-Fluoro-4-methylphenyl)(1-methylpiperidin-4-yloxy)methyl]-4-trifluoromethylpyridine
2,3-Difluoro-6-[(5-fluoropyridin-2-yl)(1-methyl piperidin-4-yloxy)methyl]phenol
6-[(5-Chloropyridin-2-yl)(1-methyl piperidin-4-yloxy)methyl]-2,3-difluorophenol
(6-{3-[(1-Methyl piperidin-4-yloxy)pyridin-2-yl methyl]phenyl}hex-5-ynyl)carbamic acid ethyl ester
6-{3-[(5-Chloropyridin-2-yl)(1-methylpiperidin-4-yloxy)methyl]phenyl}hex-5-ynylamine
2-[(1-Methylpiperidin-4-yloxy)pyridin-2-ylmethyl]phenol
5-Fluoro-2-[(5-fluoropyridin-2-yl)(1-methylpiperidin-4-yloxy)methyl]phenol
2-Fluoro-6-[(5-fluoropyridin-2-yl)(1-methylpiperidin-4-yloxy)methyl]-3-methyl phenol
6-[(5-Chloropyridin-2-yl)(1-methyl piperidin-4-yloxy)methyl]-2-fluoro-3-methylphenol
2-[(5-Chloropyridin-2-yl)(1-methylpiperidin-4-yloxy)methyl]-5-fluorophenol
2-[(5-Fluoropyridin-2-yl)(1-methylpiperidin-4-yloxy)methyl]-5-methylphenol
2-[(5-Chloropyridin-2-yl)(1-methylpiperidin-4-yloxy)methyl]-5-methylphenol
2-Fluoro-6-[(4-fluoropyridin-2-yl)(1-methylpiperidin-4-yloxy)methyl]-3-methyl phenol
4-[(3-Iodophenyl)-p-tolylmethoxy]-1-methylpiperidine
4-[(2-Fluoro-5-trifluoromethoxyphenyl)naphthalen-2-yl-methoxy]-1-methylpiperidine
4-[(2-Fluoro-4-methylphenyl)naphthalen-2-yl-methoxy]-1-methylpiperidine
4-[(3,4-Dichlorophenyl)(2-fluoro-4-methylphenyl)methoxy]-1-methylpiperidine
4-[(3,4-Dichlorophenyl)(2-fluoro-5-trifluoromethoxyphenyl)methoxy]-1-methylpiperidine
4-[(2-Fluorophenyl)-(2-fluoro-5-trifluoromethoxyphenyl)methoxy]-1-methylpiperidine
4-[(4-Chlorophenyl)(2-fluoro-5-trifluoromethoxyphenyl)methoxy]-1-methylpiperidine
4-[(4-Chlorophenyl)(2-fluoro-4-methylphenyl)methoxy]-1-methylpiperidine
4-[(4-Chlorophenyl)(3-iodophenyl)methoxy]-1-methylpiperidine
6-{3-[(4-Chlorophenyl)(1-methylpiperidin-4-yloxy)methyl]phenyl}hex-5-ynylamine
2-[(3-Iodophenyl)(1-methylpiperidin-4-yloxy)methyl]pyridine
as well as its enantiomers, diastereomers, mixtures thereof and pharmaceutically acceptable salts, tautomers, hydrates and solvates.
Unless specified otherwise, the terms used hereabove or hereafter have the meaning ascribed to them below:
"halogen" refers to fluorine, chlorine, bromine or iodine atom.
"alkyl" represents an aliphatic-hydrocarbon group which may be straight or branched having 1 to 8 carbon atoms in the chain unless specified otherwise. Preferred alkyl groups have 1 to 6 carbon atoms in the chain. Branched means that one or more alkyl groups such as methyl, ethyl or propyl are attached to a linear alkyl chain. Exemplary alkyl groups include methyl, ethyl, n-propyl, i-propyl, n-butyl, t-butyl, 2,2-dimethylbutyl, n-pentyl, n-hexyl, octyl.
"alkenyl" refers to an aliphatic hydrocarbon group containing a carbon-carbon double bond and which may be straight or branched having 2 to 8 carbon atoms in the chain unless specified otherwise. Preferred alkenyl groups have 2 to 6 carbon atoms in the chain. Exemplary alkenyl groups include ethenyl, n-propenyl, i-propenyl, n-butenyl, i-butenyl, 2,2-dimethylbut-1-enyl, n-pentenyl, heptenyl, octenyl.
"alkynyl" refers to an aliphatic hydrocarbon group containing a carbon-carbon triple bond and which may be straight or branched having 2 to 8 carbon atoms in the chain unless specified otherwise. Preferred alkynyl groups have 2 to 6 carbon atoms in the chain. Exemplary alkynyl groups include ethynyl, propynyl, n-butynyl, 2-butynyl, 3-methyl-1-butynyl, n-pentynyl, heptynyl, octynyl.

"cycloalkyl" refers to a saturated non-aromatic monocyclic hydrocarbon ring system of 3 to 10 carbon atoms. Preferred ring sizes of rings of the ring system include 3 to 8 ring atoms. Exemplary monocyclic cycloalkyl include cyclopropyl, cyclopentyl, cyclohexyl, and the like.

"cycloalkenyl" refers to a cycloalkyl as herein described containing a carbon-carbon double bond. Exemplary cycloalkenyl include cyclopentenyl, cyclohexenyl, cycloheptenyl, and the like.

"aryl" refers to an aromatic monocyclic or multicyclic hydrocarbon ring system of 6 to 14 carbon atoms, preferably of 6 to 10 carbon atoms. Exemplary aryl groups include phenyl, naphthyl, phenanthryl.

"heterocycle" or "heterocyclyl" refer to a saturated or partially unsaturated non aromatic stable 3 to 14, preferably 5 to 10-membered mono, bi or multicyclic rings which can optionally be bridged and wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics,* 76th Edition, CRC Press, Inc., 1995-1996, pages 2-25 to 2-26, the disclosure of which is hereby incorporated by reference. Preferred heterocyclyl include, but are not limited to tetrahydropyridyl, tetrahydrofuranyl, dioxolanyl, tetrahydropyranyl, dioxanyl, pyrrolidinyl, piperidyl, morpholinyl, imidazolidinyl, pyranyl, dihydropyranyl, thiopyranyl, dihydrothiopyranyl, 8-aza-bicyclo[3.2.1]oct-3-yl, azetidin-3-ylmethyl, piperidin-4-yl, pyrrolidin-3-yl, quinoclidin-3-yl, benzodioxole. Preferred heterocycles are chosen from piperidyl, tetrahydropyridyl, dihydropyranyl, dihydrothiopyranyl, 8-aza-bicyclo[3.2.1]oct-3-yl, azetidin-3-ylmethyl, piperidin-4-yl, pyrrolidin-3-yl, quinoclidin-3-yl, benzodioxole.

"heteroaryl" refers to a 5 to 14, preferably 5 to 10 membered aromatic mono-, bi- or multicyclic ring wherein at least one member of the ring is a hetero atom. Examples include pyrrolyl, pyridyl, piperidinyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, oxazolyl.

"aralkyl" refers to an arylalkyl group, the "aryl" and "alkyl" groups being as herein described.

"sulfanyl" refers to a radical —S—.

"sulfinyl" refers to a radical —SO—.

"sulfonyl" refers to a radical —$SO_2$—.

"ureido" refers to a radical NH—CO—$NH_2$. This radical can be linked for example to an alkyl or cycloalkyl group as herein described.

"thioureido" refers to radical —NH—S—$NH_2$. This radical can be linked for example to an alkyl or cycloalkyl group as herein described.

"guanidino" refers to a radical:

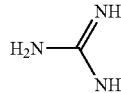

The compounds of formula (I) can comprise one or more asymmetric carbon atoms. They can therefore exist in the form of enantiomers or diastereoisomers. These enantiomers and diastereoisomers, as well as their mixtures, including racemic mixtures, form part of the invention.

The compounds of formula (I) can be provided in the form of a free base or in the form of addition salts with acids, which also form part of the invention.

These salts are advantageously prepared with pharmaceutically acceptable acids, but salts with other acids, useful for example for the purification or for the isolation of the compounds of formula (I), also form part of the invention.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylene; amides, such as N,N-dimethylformamide; alcohols such as ethanol and methanol and ethers, such as diethyl ether, methyl tert-butyl ether, methyl cyclopentyl ether and tetrahydrofuran.

The reactions can take place over a wide range of temperatures. In general, we find it convenient to carry out the reaction at a temperature of from 0° C. to 155° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 1 hour to 24 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography, preparative HPLC or preparative thin layer chromatography.

According to a first embodiment of the process of the invention, compounds of formula (I) can be prepared by condensing an alcohol of formula (III) in which R, Het and A are as defined in general formula (I) with an alcohol of formula (IV) in which R2, R3, R4, R5, R6, X7, X8, X9 and X10 are as defined in general formula (I):

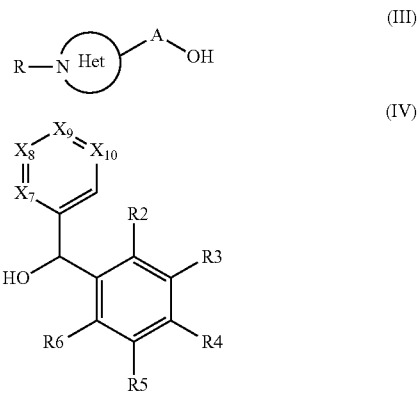

This reaction can be performed with an acidic catalyst such as p-toluenesulfonic acid, methanesulfonic acid in 1,2-dichloroethane, toluene, N-methyl-2-pyrrolidinone or a mixture thereof at a temperature comprised between −20° C. and 155° C.

According to a second embodiment, compounds of formula (I) can be obtained by condensing an alcohol of formula (III) in which R, Het and A are as defined in general formula (I) with an alkylating agent of formula (V) in which R2, R3, R4, R5, R6, X7, X8, X9 and X10 are as defined in general formula (I) and X represent a halogen or another leaving group such as a mesylate, a triflate, a nosylate or a tosylate

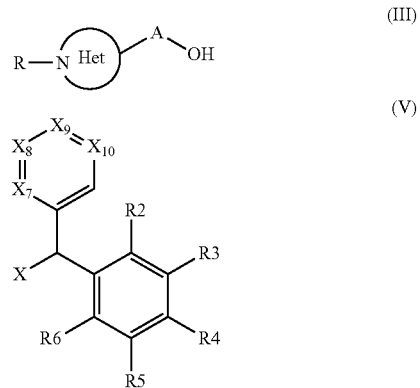

This reaction is typically performed in an inert solvent such as acetone, acetonitrile, dichloromethane, toluene at a temperature comprised between room temperature and refluxing temperature, and in the optional presence of an organic or inorganic base such as triethylamine, potassium carbonate.

Alternatively, compounds of formula (I) can be prepared from compounds of formula (I) by functional group elaboration. Such transformations include:

reacting a primary or secondary amine present in a substituent onto a chloroformate to give a carbamate, this reaction can be performed in an inert solvent such a dichloromethane at a temperature comprised between 0° C. and the reflux temperature reacting an aromatic halogen, present on an aromatic part represented by Ar or Ar", with an acetylenic compound in the presence of palladium and copper in an inert solvent such as N-methyl-2-pyrrolidinone at a temperature comprised between 60° C. and 140° C.

Compounds of formula (V) in which R2, R3, R4, R5, R6, X7, X8, X9 and X10 are as defined in general formula (I) and X represent a halogen or another leaving group such as a mesylate, a triflate, a nosylate or a tosylate can be prepared from compounds of formula (IV) in which R2, R3, R4, R5, R6, X7, X8, X9 and X10 are as defined in general formula (I):

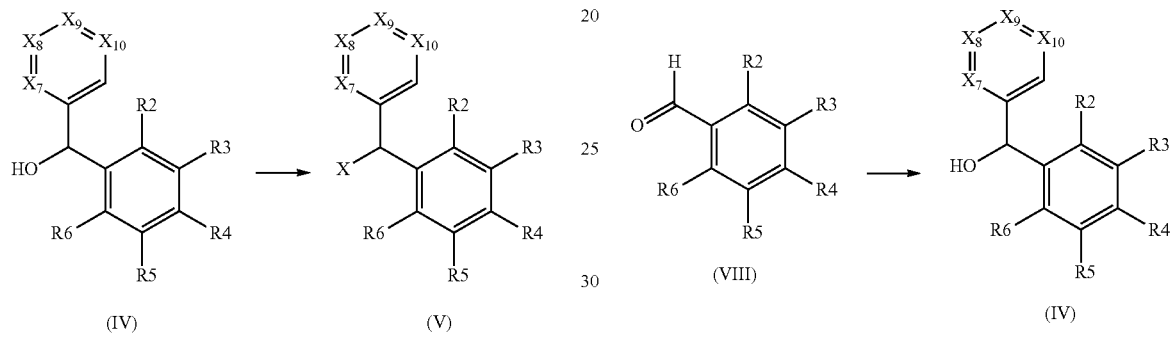

(IV) (V)

This reaction can be performed with an halogenating agent such as thionyl chloride, phosphorus pentabromide or a sulfonate derivative such as mesyl chloride, triflic anhydride, nosyl chloride or tosyl chloride in an inert solvent such as acetone, acetonitrile, dichloromethane, toluene at a temperature comprised between 0° C. and refluxing temperature, in the optional presence of an organic or inorganic base such as triethylamine, diisopropylethylamine or potassium carbonate.

Compounds of formula (IV) in which R2, R3, R4, R5, R6, X7, X8, X9 and X10 are as defined in general formula (I) can be obtained by either of the following routes i, ii or iii:

i. by reduction of the corresponding ketone (VI) in which R2, R3, R4, R5, R6, X7, X8, X9 and X10 are as defined in general formula (I):

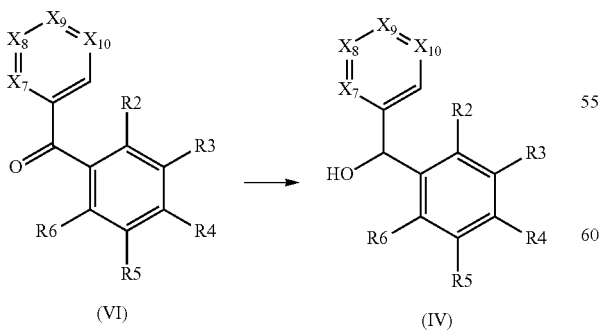

(VI) (IV)

ii. from a corresponding aldehyde (VII) in which X7, X8, X9 and X10 are as defined in general formula (I):

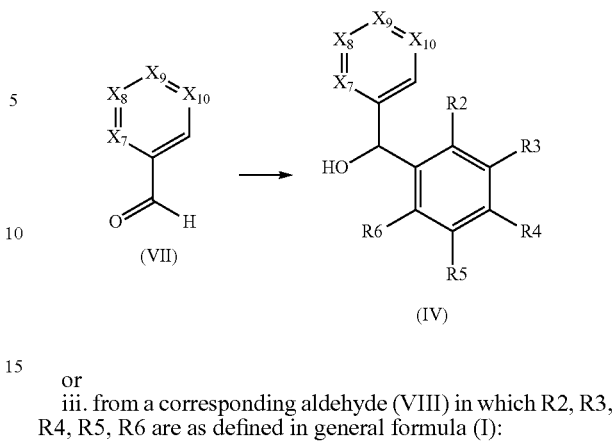

or iii. from a corresponding aldehyde (VIII) in which R2, R3, R4, R5, R6 are as defined in general formula (I):

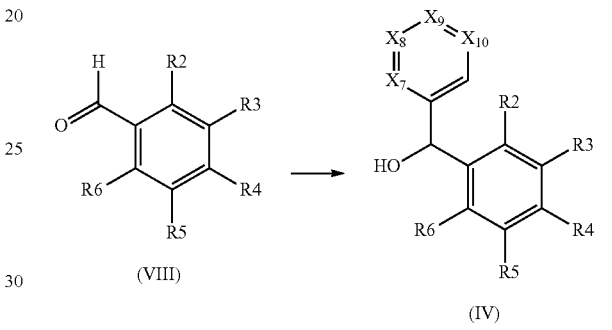

Reaction i. can be performed in the presence of a reducing agent such as a borohydride in an alcohol at a temperature comprised between 0° C. and the refluxing temperature.

Reaction ii. can be performed by reacting the aldehyde (VII) with the corresponding compound of formula (IX):

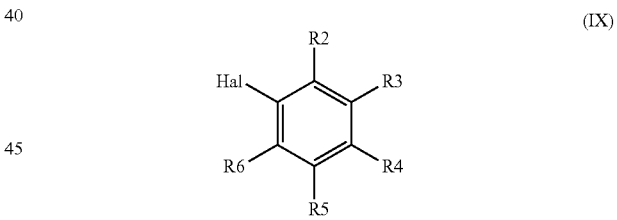

in which R2, R3, R4, R5, R6 are as defined in general formula (I) and Hal represents a halogen atom, in the presence of an organometallic reagent such as an organomagnesium (e.g. n-butylmagnesium chloride, isopropylmagnesium chloride, etc.) or organolithium (e.g. butyllithium, etc. . . . )

or with the corresponding compound of formula (IX'):

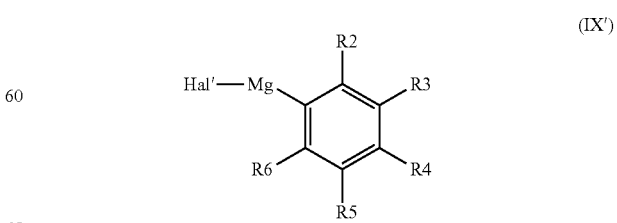

in which R2, R3, R4, R5, R6 are as defined in general formula (I) and Hal' represents a halogen atom, in an inert solvent such as tetrahydrofuran at a temperature comprised between −78° C. and the reflux temperature.

Alternatively, reaction ii. can also be performed by condensing the aldehyde (VII) with the corresponding derivative of formula (IX")

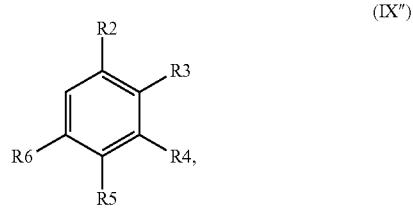

(IX")

in which R2, R3, R4, R5, R6 are as defined in general formula (I), in the presence of a lewis acid catalyst such as aluminum trichloride in an inert solvent such as dichloromethane at a temperature comprised between 0° C. and reflux temperature.

Reaction iii. can be performed by reacting the aldehyde (VIII) with the corresponding compound of formula (X):

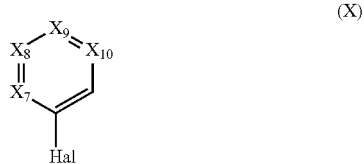

(X)

Where X7, X8, X9 and X10 are as defined in formula (I) and Hal represents a halogen atom, in the presence of an organometallic reagent such as an organomagnesium (e.g. n-butylmagnesium chloride, isopropylmagnesium chloride, etc.) or organolithium (e.g. butyllithium, etc. . . . ), or with the corresponding compound of formula (X'):

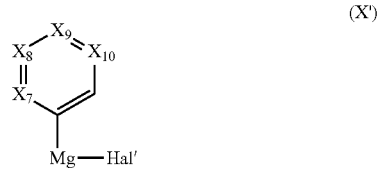

(X')

where X7, X8, X9 and X10 are as defined in formula (I) and Hal' represents a halogen atom in an inert solvent such as tetrahydrofuran at a temperature comprised between −78° C. and the reflux temperature.

The process of the invention may comprise the additional step of isolating the desired compound of formula (I).

According to a still further object, the present invention is also concerned with pharmaceutical compositions comprising a compound of formula (I) as defined above with a pharmaceutically acceptable excipient.

The compounds of the invention are antagonists and/or inverse agonists of H4 R. The pharmaceutical compositions and compounds of the invention may thus be useful for use in the treatment and/or prevention of a disease associated with $H_4$ dysfunction, such as inflammatory disorders.

Said disease includes adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy induced airway responses, allergic rhinitis, viral rhinitis, non-allergic rhinitis, perennial and seasonal rhinitis, conjunctivitis, nasal congestion, allergic congestion; disorders of the genito-urinary tract such as female and male sexual dysfunction, overactive bladder conditions, urinary incontinence, bladder overactivity, benign prostate hyperplasia and lower urinary tract symptoms; dermatological diseases such as dermatitis and psoriasis and treatment of itchy skin; diseases of the cardiovascular system including thromboembolic diseases, atherosclerosis, myocardial infarction, angina pectoris, myocardial ischaemia and arrhythmia, peripheral arterial occlusive diseases, pulmonary embolisms or deep venous thromboses, hypotension, pulmonary hypertension, malignant hypertension, cardiac insufficiency, heart or kidney failure, stroke and renal dysfunction; diseases of the gastrointestinal tract including inflammatory bowel disease, Crohn's disease, ulcerative colitis; autoimmune diseases including rheumatoid arthritis, multiple sclerosis; cancer; pain; lymphatic diseases.

According to a further object, the present invention also concerns a combination of a compound of the invention with one or more therapeutic agent(s) selected from:

Histamine $H_1$, $H_2$ or $H_3$ receptor antagonists,
Leukotriene antagonists,
5-Lipoxygenase (5-LO) inhibitors or 5-lipoxygenase activating protein (FLAP) antagonists
$CX_1$- and $\alpha_2$-adrenoceptor agonist vasoconstrictor sympathomimetic agents for decongestant use
Xanthines, such as theophylline and aminophylline
Non-steroidal antiinflammatories, such as sodium cromoglycate and nedocromil sodium
Ketotifen
COX-1 inhibitors (NSAIDs) and COX-2 selective inhibitor
Immunosuppressants
mucolytics or anti-tussive agents.

More particularly, the present invention also concerns combinations comprising a compound of formula (I) of the invention with a H1R antagonist, such as cetirizine, levocetirizine, desloratadine, bepotastine or doxepin.

According to a still further object, the present invention is also concerned with a compound of formula (I) for the above conditions to be administered to a patient in the need thereof.

According to a still further object, the present invention also concerns the methods of treatment comprising administering an effective amount of a compound of the invention for treating and/or preventing the above conditions or disorders.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day. A preferred daily dose for adult humans includes 1, 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably, the unit dose range is from 1 to 500 mg administered one to four times a day, and even more preferably from 1 mg to 300 mg, once a day. Compounds provided herein can be formulated into pharmaceutical compositions by admixture with one or more pharmaceutically acceptable excipients. Such compositions may be prepared for use in oral administration, particularly in the form of tablets or capsules, in particular orodispersible (lyoc) tablets; or parenteral administration, particularly in the form of liquid solutions, suspensions or emulsions; or intranasally, particularly in the form of powders, nasal drops, or aerosols; or dermally, for example, topically or via trans-dermal patches or ocular administration, or intravaginal or intra-uterine administration, particularly in the form of pessaries or by rectal administration.

The compositions may conveniently be administered in unit dosage form and may be prepared by any of the methods well known in the pharmaceutical art, for example, as described in Remington: *The Science and Practice of Pharmacy*, 20$^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

Other features of the invention will become apparent in the course of the following description of exemplary embodiments that are given for illustration of the invention and not intended to be limiting thereof.

ACRONYMS

RT: retention time

EXAMPLES

Melting points are determined on Büchi capillary melting point apparatus.

Proton NMR spectra are recorded on a Bruker 250 MHz NMR instrument. The chemicals shifts δ are expressed in ppm. The following abbreviations are used to denote signal patterns: s=singlet, d=doublet, t=triplet, q=quadruplet, m=multiplet, ms=massif. The coupling contents are expressed in Hz. The spectra recorded are consistent with the proposed structures.

HPLC-MS analyses are performed on a Waters AutoPurification HPLC/MS System equipped with a 3100 Mass Spectrometer and a 2998 Photodiode Array (PDA) Detector.

The MS spectra recorded are consistent with the proposed structures.

The LC retention times are obtained using the following elution conditions:
LC/MS Method A: Xterra MS C18 5 µm 2.1×10 mm guard column, Xterra MS C18 5 µm 3.0×100 mm column, eluents: water/0.1% formic acid (A) and acetonitrile/0.1% formic acid (B), linear gradient from 5% (B) to 95% (B) in 6 minutes.
LC/MS Method E: Sunfire C18 5 µm 4.6×20 mm guard column, Sunfire C18 5 µm 4.6×150 mm column, eluents: water/0.1% formic acid (A) and acetonitrile/0.1% formic acid (B), linear gradient from 5% (B) to 95% (B) in 10 minutes.

Example 1

2-[(2-Fluoro-5-trifluoromethoxyphenyl)(1-methylpiperidin-4-yloxy)methyl]pyridine, dioxalate

1A

A mixture of (2-fluoro-5-trifluoromethoxyphenyl)pyridin-2-ylmethanol (340 mg) and 4-hydroxy-1-methylpiperidine (273 mg) in methanesulfonic acid (1.5 mL) is heated in a sealed tube at 145° C. for 24 hours and then at 155° C. for 7 hours. The mixture is cooled back to room temperature, poured into water which is then made alkaline with concentrated sodium hydroxide solution. The aqueous phase is extracted with diethyl ether. Pooled extracts are dried over magnesium sulphate and concentrated under reduced pressure. The residue is purified by column chromatography over silica gel (gradient dichloromethane/methanol/ammonia from 95/5/0.5 to 90/10/0.5) to afford the pure base that is then converted into its dioxalate salt in acetone to give 2-[(2-fluoro-5-trifluoromethoxyphenyl)(1-methylpiperidin-4-yloxy)methyl]pyridine, dioxalate melting at 45° C.

1B

To a solution of 2-bromopyridine (380 mg) in anhydrous tetrahydrofuran (3 mL) is slowly added a 1M solution of isopropylmagnesium bromide in tetrahydrofuran (2.64 mL) at room temperature. After stirring for 2 hours, 2-fluoro-5-(trifluoromethoxy)benzaldehyde (0.50 mL) is added and the reaction mixture stirred for 2 hours. After hydrolysis with water and 3N hydrochloric acid, the mixture is washed with diethyl ether, basified with concentrated sodium hydroxide and extracted with ethyl acetate twice. The pooled organic extracts are dried over magnesium sulfate and concentrated under reduced pressure. The residue is purified by chromatography over silica gel (heptane/ethyl acetate 2/1) to afford (2-fluoro-5-trifluoromethoxyphenyl)pyridin-2-ylmethanol as an orange oil.

Further examples can be prepared according to example 1. As regards the etherification step it can be advantageous to rise the temperature progressively after having mixed the different reagents and to observe when etherification occurs. Once the right temperature has been found, reaction may be continued up to adequate conversion.

| Ex. | Name | Melting point | RT (min) HPLC/MS method |
|---|---|---|---|
| 2 | 5-Chloro-2-[(2-fluoro-4-methylphenyl)(1-methylpiperidin-4-yloxy)methyl]pyridine, oxalate | 165° C. | |
| 3 | 2-[(2-Fluoro-4-methylphenyl)(1-methylpiperidin-4-yloxy)methyl]pyridine, dioxalate | 59° C. | |
| 4 | 5-Chloro-2-[(2-fluoro-5-trifluoromethoxyphenyl)(1-methylpiperidin-4-yloxy)methyl]pyridine, oxalate | 75° C. | |
| 37 | 2-[(3-Iodophenyl)(1-methylpiperidin-4-yloxy)methyl]pyridine, oxalate | | 3.65 Method A |

Example 5

6-{3-[(1-Methylpiperidin-4-yloxy)pyridin-2-ylmethyl]phenyl}hex-5-ynylamine, oxalate

5A

A solution of 2-(6-{3-[(1-methylpiperidin-4-yloxy)-pyridin-2-ylmethyl]phenyl}hex-5-ynyl)isoindole-1,3-dione (205 mg) and hydrazine hydrate (150 µL) in ethanol (1.5 mL) is stirred a room temperature for 2 hours. Ethanol is removed under reduced pressure and the residue purified by chromatography over silica gel (gradient dichloromethane/methanol/ammonia from 95/5/0.5 to 90/10/0.5) to afford the pure base that is then converted into its oxalate salt in acetone to give 6-{3-[(1-methylpiperidin-4-yloxy)pyridin-2-ylmethyl]phenyl}hex-5-ynylamine, oxalate displaying the following NMR spectrum: $^1$H NMR (DMSO-d$^6$): 8.44 (d, 1H), 7.79 (t, 1H), 7.55 (d, 1H), 7.35-7.22 (ms, 5H), 5.61 (s, 1H), 2.90-2.70 (ms, 6H), 2.42 (m, 2H), 2.34 (s, 3H), 1.88 (m, 2H), 1.62 (m, 6H). Missing signals are masked by deuterated solvents peaks.

5B

A screw-cap tube is charged with 2-[(3-iodophenyl)(1-methylpiperidin-4-yloxy)methyl]pyridine (105 mg, example 37), tetrakis(triphenylphosphine)palladium (52 mg), copper (I) iodide (26 mg), N-5-hexynylphthalimide (186 mg), triethylamine (400 µL) and 1-methyl-2-pyrrolidinone (4 mL). The tube is evacuated, filled with argon and sealed. After stirring at 90° C. for 14 h, the mixture is diluted with water and the aqueous phase is extracted with ethyl acetate. The pooled organic extracts are washed with water, dried over magnesium sulfate and concentrated under reduced pressure. The residue is purified by chromatography over silica gel (gradient dichloromethane/methanol/ammonia from 98/2/0.5 to 95/5/0.5) to give 2-(6-{3-[(1-methylpiperidin-4-yloxy)-pyridin-2-ylmethyl]phenyl}hex-5-ynyl)isoindole-1,3-dione as an brown oil.

Example 6

4-[(2-Fluoro-5-trifluoromethoxyphenyl)(1-methylpiperidin-4-yloxy)methyl]pyridine, dioxalate

6A

4-[(2-Fluoro-5-trifluoromethoxyphenyl)(1-methylpiperidin-4-yloxy)methyl]pyridine, dioxalate, solid melting at 61°

C., is prepared according general procedure 1A from (2-fluoro-5-trifluoromethoxyphenyl)pyridin-4-ylmethanol.

6B

To a solution in tetrahydrofuran (3 mL) at 0° C. of 2.3M n-butyllithium in hexanes (0.95 mL) and 2M n-butylmagnesium chloride in tetrahydrofuran (0.55 mL) is added a solution of 2-bromo-1-fluoro-4-trifluoromethoxybenzene in tetrahydrofuran (4 mL). After stirring at 0° C. for 20 minutes 4-pyridinecarboxaldehyde (193 µL) is added and the mixture stirred at room temperature for one night. After hydrolysis with water, the aqueous phase is extracted with ethyl acetate. The pooled organic extracts are washed with water, dried over magnesium sulfate and concentrated under reduced pressure. The residue is purified by chromatography over silica gel (gradient heptane/ethyl acetate from 2/1 to 1/1) to give pure (2-fluoro-5-trifluoromethoxyphenyl)pyridin-4-ylmethanol.

Example 7

2-[(2-Fluoro-4-methylphenyl)(1-methylpiperidin-4-yloxy)methyl]-4-methylpyridine, dioxalate

7A

2-[(2-Fluoro-4-methylphenyl)(1-methylpiperidin-4-yloxy)methyl]-4-methylpyridine, dioxalate, solid melting at 52° C., is prepared analogously to example 1 from (2-fluoro-4-methylphenyl)(4-methylpyridin-2-yl)methanol.

7B

To a solution of 2-bromo-4-methylpyridine (600 mg) in diethyl ether (20 mL) at −78° C. is added a 2.3M solution of butyllithium in hexanes (1.52 mL). After stirring at this temperature for 1 hour 2-fluoro-4-methylbenzaldehyde is added and the mixture allowed to warm at room temperature. The reaction mixture is then hydrolyzed with diluted aqueous hydrochloric acid, washed with diethyl ether, basified with concentrated sodium hydroxide and extracted with diethyl ether. The pooled organic extracts are dried over magnesium sulfate and concentrated under reduced pressure. The residue is purified by chromatography over silica gel (heptane/ethyl acetate 2/1) to afford (2-fluoro-4-methylphenyl)(4-methylpyridin-2-yl)methanol as a pale yellow oil which solidifies on standing.

Further examples can be prepared according to example 7. As regards the etherification step it can be advantageous to rise the temperature progressively after having mixed the different reagents and to observe when etherification occurs. Once the right temperature has been found, reaction may be continued up to adequate conversion.

| Ex. | Name | Melting point | RT (min) HPLC/MS method |
|---|---|---|---|
| 8 | 2-[(2-Fluoro-5-trifluoromethoxyphenyl)(1-methylpiperidin-4-yloxy)methyl]-4-methylpyridine, dioxalate | 43° C. | |
| 9 | 5-Chloro-2-[(4-chlorophenyl)(1-methylpiperidin-4-yloxy)methyl]pyridine, oxalate | 190° C. | |
| 10 | 5-Fluoro-2-[(2-fluoro-4-methylphenyl)(1-methylpiperidin-4-yloxy)methyl]pyridine, oxalate | 133° C. | |
| 11 | 5-Fluoro-2-[(2-fluoro-5-trifluoromethoxyphenyl)(1-methylpiperidin-4-yloxy)methyl]pyridine, oxalate | 113° C. | |
| 12 | 5-Chloro-2-[(3-methoxyphenyl)(1-methylpiperidin-4-yloxy)methyl]pyridine, oxalate | 175° C. | |
| 13 | 5-Chloro-2-[(3-iodophenyl)(1-methylpiperidin-4-yloxy)methyl]pyridine, oxalate | 130° C. | |
| 14 | 2-[(2-Fluoro-4-methylphenyl)(1-methylpiperidin-4-yloxy)methyl]-4-trifluoromethylpyridine, oxalate | 104° C. | |
| 15 | 2,3-Difluoro-6-[(5-fluoropyridin-2-yl)(1-methylpiperidin-4-yloxy)methyl]phenol | 73° C. | 3.76 Method A |
| 16 | 6-[(5-Chloropyridin-2-yl)(1-methylpiperidin-4-yloxy)methyl]-2,3-difluorophenol | 68° C. | 3.91 Method A |

Example 17

(6-{3-[(1-Methylpiperidin-4-yloxy)pyridin-2-ylmethyl]phenyl}hex-5-ynyl)carbamic acid ethyl ester, oxalate To a solution of 6-{3-[(1-methylpiperidin-4-yloxy)pyridin-2-ylmethyl]phenyl}hex-5-ynylamine (28 mg, example 5) in dichloromethane (1 mL) is added a solution of ethyl chloroformate (142 µL) in dichloromethane (2 mL) at 0° C. After stirring at room temperature for one night, the reaction mixture is treated with 1N sodium hydroxide. The organic phase is then submitted to chromatography over silica gel (gradient dichloromethane/methanol from 99/1 to 95/5) to afford the pure base that is then converted into its oxalate salt in ethanol to give (6-{3-[(1-methylpiperidin-4-yloxy)pyridin-2-ylmethyl]phenyl}hex-5-ynyl)carbamic acid ethyl ester, oxalate as a solid melting at 77° C.

Example 18

6-{3-[(5-Chloropyridin-2-yl)(1-methylpiperidin-4-yloxy)methyl]phenyl}hex-5-ynylamine, oxalate 6-{3-[(5-Chloropyridin-2-yl)(1-methylpiperidin-4-yloxy)methyl]phenyl}hex-5-ynylamine, oxalate, solid melting at 136° C., is prepared analogously to example 5 starting from example 13.

Example 19

2-[(1-Methyl piperidin-4-yloxy)pyridin-2-ylmethyl]phenol, oxalate

19A

A mixture of 2-(hydroxypyridin-2-ylmethyl)phenol (0.27 g), 4-hydroxy-1-methylpiperidine (0.31 g) and para-toluenesulfonic acid, monohydrate (0.89 g) in toluene (20 mL) and 1-methyl-2-pyrrolidinone (1 mL) is heated for 3 hours in a Dean-Stark apparatus. The mixture is cooled back to room temperature, treated with aqueous NaHCO₃ and extracted twice with ethyl acetate. Pooled organic extracts are washed with brine, dried over magnesium sulfate and concentrated. The residue is purified by column chromatography over silica gel (gradient dichloromethane/methanol/ammonia from 100/

0/0.5 to 95/5/0.5) to afford the pure base that is then converted into its oxalate salt in acetone to give 2-[(1-methylpiperidin-4-yloxy)pyridin-2-ylmethyl]phenol, oxalate as a solid melting at 70° C.

19B

To a solution of AlCl3 (1.42 g) in dichloromethane (20 mL) at 0° C. is added a solution of phenol (1 g) in dichloromethane (20 mL) and the mixture is stirred at this temperature for 40 minutes. After addition of a solution of pyridine-2-carboxaldehyde (1.21 g) in dichloromethane (10 mL), the mixture is allowed to warm at room temperature for 4 hours, then cooled to 0° C., treated dropwise with aqueous ammonium chloride and stirred at room temperature for 30 minutes. The aqueous phase is extracted twice with dichloromethane and pooled organic extracts dried over magnesium sulfate and concentrated. The residue is purified by column chromatography over silica gel (gradient heptane/ethyl acetate from 100/0 to 70/30) to afford pure 2-(hydroxy-pyridin-2-yl-methyl)-phenol.

Example 20

5-Fluoro-2-[(5-fluoropyridin-2-yl)(1-methylpiperidin-4-yloxy)methyl]phenol, oxalate

20A

A mixture of 5-fluoro-2-[(5-fluoropyridin-2-yl)hydroxymethyl]phenol (100 mg), 4-hydroxy-1-methylpiperidine (97 mg), methanesulfonic acid (109 µL) in 1,2-dichloroethane (3 mL) is heated for 1 hour at 80° C. The mixture is cooled back to room temperature, slowly basified with a saturated aqueous sodium hydrogencarbonate solution and extracted with dichloromethane. Pooled extracts are dried over magnesium sulphate and concentrated under reduced pressure. The residue is purified by column chromatography over silica gel (gradient dichloromethane/methanol/ammonia from 95/5/0.5 to 90/10/0.5) to afford the pure base that is then converted into its oxalate salt in acetone to give 5-fluoro-2-[(5-fluoropyridin-2-yl)(1-methylpiperidin-4-yloxy)methyl]phenol, oxalate melting at 105° C. HPLC-MS method A, RT=3.66 min.

20B

5-Fluoro-2-[(5-fluoropyridin-2-yl)hydroxymethyl]phenol is prepared according to general procedure 7B of example 7 with a supplementary equivalent of lithiated pyridine.

Further examples can be prepared according to example 20. As regards the etherification step it can be advantageous to rise the temperature progressively after having mixed the different reagents and to observe when etherification occurs. Once the right temperature has been found, reaction may be continued up to adequate conversion. 1-Methyl-2-pyrrolidinone can be added to the mixture to ensure total solubility of the reagents.

| Ex. | Name | Melting point | RT (min) HPLC/MS method |
|---|---|---|---|
| 21 | 2-Fluoro-6-[(5-fluoropyridin-2-yl)(1-methylpiperidin-4-yloxy)methyl]-3-methylphenol | 62° C. | 3.82 Method A |
| 22 | 6-[(5-Chloropyridin-2-yl)(1-methylpiperidin-4-yloxy)methyl]-2-fluoro-3-methylphenol | 67° C. | 3.96 Method A |
| 23 | 2-[(5-Chloropyridin-2-yl)(1-methylpiperidin-4-yloxy)methyl]-5-fluorophenol | 57° C. | 5.07 Method E |
| 24 | 2-[(5-Fluoropyridin-2-yl)(1-methylpiperidin-4-yloxy)methyl]-5-methylphenol, oxalate | 77° C. | 3.74 Method A |
| 25 | 2-[(5-Chloropyridin-2-yl)(1-methylpiperidin-4-yloxy)methyl]-5-methylphenol, oxalate | 77° C. | 3.95 Method A |
| 26 | 2-Fluoro-6-[(4-fluoropyridin-2-yl)(1-methylpiperidin-4-yloxy)methyl]-3-methylphenol | 64° C. | 3.70 Method A |

Example 27

4-[(3-Iodophenyl)-p-tolylmethoxy]-1-methylpiperidine, oxalate

27A

A mixture of chloro-(3-iodophenyl)-p-tolylmethane (2.47 g), 4-hydroxy-1-methylpiperidine (1.66 g) in acetonitrile is refluxed for one night. Solvent is then removed under reduced pressure and the residue diluted with water, 0.5N aqueous sodium hydroxide and ethyl acetate. The organic phase is dried over magnesium sulfate, concentrated and the residue purified by column chromatography over silica gel (gradient dichloromethane/methanol from 100/0 to 90/10) to afford the pure base that is then converted into its oxalate salt in acetone to give 4-[(3-iodophenyl)-p-tolylmethoxy]-1-methylpiperidine, oxalate, a solid melting at 60° C.

27B

To a solution of (3-iodophenyl)-p-tolylmethanol (2.68 g) in dichloromethane (50 mL) at 0° C. is slowly added thionyl chloride (633 µL). After stirring at room temperature for 2 days, the mixture is washed with aqueous NaHCO₃, dried over magnesium sulfate and concentrated under reduced pressure to afford chloro-(3-iodophenyl)-p-tolylmethane.

27C

To a solution of 3-iodobenzaldehyde (10 g) in tetrahydrofuran (50 mL) at 30° C. is added a 0.43M solution of p-tolylmagnesium bromide in tetrahydrofuran. After stirring at 50° C. for 1 hour, the reaction mixture is hydrolyzed with a saturated aqueous solution of ammonium chloride and extracted ethyl acetate. Pooled organic extracts are washed with brine, dried over magnesium sulfate and concentrated. The residue is purified by column chromatography over silica gel (gradient heptane/ethyl acetate 95/5 to 90/10) to yield (3-iodophenyl)-p-tolylmethanol.

Example 28

4-[(2-Fluoro-5-trifluoromethoxyphenyl)naphthalen-2-ylmethoxy]-1-methylpiperidine, oxalate 4-[(2-Fluoro-5-trifluoromethoxyphenyl)naphthalen-2-ylmethoxy]-1-methylpiperidine, oxalate, solid melting at 105° C., is prepared analogously to example 27.

Example 29

4-[(2-Fluoro-4-methylphenyl)naphthalen-2-yl-methoxy]-1-methylpiperidine, oxalate 4-[(2-Fluoro-4-methylphenyl)naphthalen-2-yl-methoxy]-1-methylpiperidine, oxalate, solid melting at 122° C., is prepared analogously to example 27.

Example 30

4-[(3,4-Dichlorophenyl)(2-fluoro-4-methylphenyl)methoxy]-1-methylpiperidine, oxalate 4-[(3,4-Dichlorophenyl)(2-fluoro-4-methylphenyl)methoxy]-1-methylpiperidine, oxalate, solid melting at 140° C., is prepared according general procedures 1A (a few seconds at room temperature) and 6B from 3,4-dichlorobenzaldehyde and 1-bromo-2-fluoro-4-methylbenzene.

Example 31

4-[(3,4-Dichlorophenyl)(2-fluoro-5-trifluoromethoxyphenyl)methoxy]-1-methylpiperidine, oxalate 4-[(3,4-Dichlorophenyl)(2-fluoro-5-trifluoromethoxyphenyl)methoxy]-1-methylpiperidine, oxalate, solid melting at 115° C., is prepared according general procedures 1A (30 seconds at 60° C.) and 6B from 3,4-dichlorobenzaldehyde and 2-bromo-1-fluoro-4-trifluoromethoxybenzene.

Example 32

4-[(2-Fluorophenyl)-(2-fluoro-5-trifluoromethoxyphenyl)methoxy]-1-methylpiperidine, oxalate 4-[(2-Fluorophenyl)-(2-fluoro-5-trifluoromethoxyphenyl)methoxy]-1-methyl piperidine, oxalate, solid melting at 116° C., is prepared according general procedures 1A (15 minutes at 5° C.) and 6B from 2-fluorobenzaldehyde and 2-bromo-1-fluoro-4-trifluoromethoxybenzene.

Example 33

4-[(4-Chlorophenyl)(2-fluoro-5-trifluoromethoxyphenyl)methoxy]-1-methylpiperidine, oxalate 4-[(4-Chlorophenyl)(2-fluoro-5-trifluoromethoxyphenyl)methoxy]-1-methyl piperidine, oxalate, solid melting at 117° C., is prepared according general procedures 1A (10 minutes at −5° C.) and 6B from 4-chlorobenzaldehyde and 2-bromo-1-fluoro-4-trifluoromethoxybenzene.

Example 34

4-[(4-Chlorophenyl)(2-fluoro-4-methylphenyl)methoxy]-1-methylpiperidine, oxalate 4-[(4-Chlorophenyl)(2-fluoro-4-methylphenyl)methoxy]-1-methylpiperidine, oxalate, solid melting at 165° C., is prepared according general procedures 1A (5 minutes at −15° C.) and 6B from 4-chlorobenzaldehyde and 1-bromo-2-fluoro-4-methylbenzene.

Example 35

4-[(4-Chlorophenyl)(3-iodophenyl)methoxy]-1-methylpiperidine, oxalate

4-[(4-Chlorophenyl)(3-iodophenyl)methoxy]-1-methylpiperidine, oxalate, solid melting at 141° C., is prepared according general procedures 1A (10 minutes at −5° C.) and 6B from 3-iodobenzaldehyde and 4-bromo-chlorobenzene.

Example 36

6-{3-[(4-Chlorophenyl)(1-methylpiperidin-4-yloxy)methyl]phenyl}hex-5-ynylamine, dioxalate 6-{3-[(4-Chlorophenyl)(1-methylpiperidin-4-yloxy)methyl]phenyl}hex-5-ynylamine, dioxalate, solid melting at 90° C., is prepared from example 35 according to general procedures 5A and 5B.

Biological Data
In Vitro Evaluation of Compounds
Membrane Preparation

SH-SY5Y cells stably expressing human H4 receptor are grown until sub-confluence and centrifuged at 300 g 15 minutes at 4° C. Pellets are resuspended in buffer I Tris-HCl 50 mM, $MgCl_2$ 10 mM, NaCl 140 mM, pH=7.4 supplemented by Leupeptin 10 µg/mL, Phenyl Methyl Sulphonyl Fluoride (PMSF) 0.1 mM, Aprotinin 2 µg/mL and Pepstatin 2 µM (or a 1/50 dilution of a mix of protease inhibitors). The obtained suspension is stirred gently and submitted to a 25-26×g mechanic pressure exerted through a syringe. The cell lysate is then centrifuged at 300 g 15 minutes at 4° C. in order to eliminate nucleus and cell scraps. The obtained supernatant is then centrifuged at 48000 g for 30 minutes at 4° C. The final pellet is resuspended in buffer I with a potter homogenizer. Aliquots are frozen in liquid nitrogen and stored until use at −80° C. Protein content is measured by the Bradford method.

GTPγ [$^{35}$S] Binding

Defreezed membranes are diluted at a final concentration of 5 µg/180 µL/well in buffer I supplemented by GDP 10 µM and distributed in 96 well polystyrene microplate. GTPγ [$^{35}$S] labelled ligand (0.2-0.3 nM) is added for additional 30 minutes. After transfer in a Millipore GF/C HTS® microplate, the filtration of the rectional mix is followed by a three times 250 µl wash to stop the reaction.

The filter-bound radioactivity is measured in a liquid scintillation counter Microbeta TRILUX® with 50 µl of scintillation fluid.

GTPγ [$^{35}$S] dependent binding activity is determined in vitro for Histamine, Imetit, R(−)-alpha-methyl-histamine and all our compounds.

Compounds can also be tested against Histamine or Imetit to evaluate their antagonist potential. Results are expressed with IC50 and Ki values.

Membrane Preparation

CHO cells stably expressing human H4 receptor were grown until sub-confluence and centrifuged at 300 g 15 minutes at 4° C. Pellets were resuspended in buffer I Tris-HCl 50 mM, MgCl$_2$ 10 mM, NaCl 140 mM, pH=7.4 supplemented by a 1/50 dilution of a mix of protease inhibitors. The obtained suspension is stirred gently and submitted to a 25-26×g mechanic pressure exerted through a syringe. The cell lysate is then centrifuged at 300 g 15 minutes at 4° C. in order to eliminate nucleus and cell scraps. The obtained supernatant was then centrifuged at 48000 g for 30 minutes at 4° C. The final pellet is resuspended in buffer I with a potter homogenizer. Aliquots were frozen in liquid nitrogen and stored until use at −80° C. Protein content is measured by the Bradford method.

[$^3$H]Histamine Binding

Defreezed membranes were diluted at a final concentration of 20 μg/180 μL/well in a binding buffer containing 50 mM Tris/HCl, 0.5 mM EDTA, pH=7.4 and distributed in 96 well polystyrene microplate. [$^3$H] Histamine labelled ligand (10-15 nM) is added for 60 minutes with compounds at room temperature under continuous stirring. Non specific binding was estimated in the presence of 10 μM BP1.2404 (JNJ 7777120). The reaction was terminated by filtration through GF/B filters pre-soaked 2 hours at 4° C. in 1% polyethyleneimine. Filters were rinsed 3 times with 250 μl of ice cold incubation binding buffer.

The filter-bound radioactivity was measured in a liquid scintillation counter Microbeta TRILUX® with 50 μl of scintillation fluid.

The hH4 binding investigated by use of [$^3$H] Histamine give a Bmax ~1 μmole/mg prot and a Kd ~9 nM.

Compounds described hereabove have been evaluated in the GTPγ [$^{35}$S] assay or in the [$^3$H] histamine binding assay and have been found active with a Ki or IC50 under 1000 nM.

| Ex | Ki | IC50 |
|---|---|---|
| 1 | B | B |
| 2 | C | B |
| 3 | B | |
| 4 | B | B |
| 5 | B | B |
| 6 | B | |
| 7 | B | B |
| 8 | B | |
| 9 | B | |
| 10 | B | B |
| 11 | A | |
| 12 | A | |
| 13 | B | |
| 14 | B | |
| 15 | A | |
| 16 | B | |
| 17 | A | |
| 18 | C | B |
| 19 | B | |
| 20 | B | |
| 21 | B | |
| 22 | C | |
| 23 | C | |
| 24 | C | |
| 25 | C | |
| 26 | B | |
| 27 | A | |
| 28 | A | B |
| 29 | | A |
| 30 | B | B |
| 31 | B | B |
| 32 | A | A |
| 33 | B | B |
| 34 | B | |
| 35 | C | B |
| 36 | C | C |
| 37 | A | |

A: Ki or IC50 <1000 nM
B: Ki or IC50 <300 nM
C: Ki or IC50 <30 nM

The invention claimed is:

1. Compounds of formula (I):

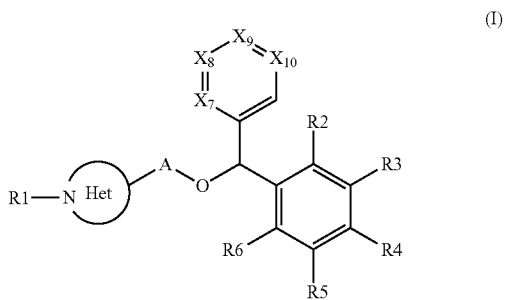

wherein

R1 represents a C1-C6 alkyl;

Het represents a piperidine wherein the nitrogen atom of the piperidine is linked to R1;

A represents a single bond attached at the 4-position of the piperidine;

each R2, R3, R4, R5, and R6 is identical or different and is independently selected from the group consisting of:
hydrogen
halo; hydroxy;
alkyl; alkoxy; alkenyl and alkynyl;
whose alkyl, alkenyl, or alkynyl part can be substituted with one or more of halo, amino, alkoxycarbonylamino, wherein at least one of R2, R3, R4, R5, or R6 is different from H;

each Xi, identical or different is chosen from —N═, —C(Ri)═ and —C(Ri')═, i representing the 7, 8, 9 or 10 indicia wherein either one of the Xi is —N═ and the others are —C(Ri)═ or either each Xi is chosen from —C(Ri)═ and —C(Ri')═ with at least of Xi being —C(Ri')═ wherein for each i said Xi may be identical or different and said Ri may be identical or different and chosen from H or Ri', provided that when

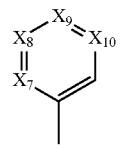

represents a substituted phenyl or an optionally substituted pyridyl, said substituent(s) are Ri' wherein said Ri' is selected from the group consisting of:
halo, cyano, alkyl optionally substituted with one or more of halo; and
aryl;
and wherein X9, R9 and R10 can form together with the C atoms to which they are attached an aromatic ring
with the exception of the compounds where simultaneously:
X9 is —CR9'=,
X7=X8=X10=—CH=,
R4 is not H and
R2=R3=R5=R6=H
as well as their enantiomers, diastereomers, mixtures thereof and pharmaceutically acceptable salts, tautomers, hydrates and solvates.

2. Compounds according to claim 1 wherein the compounds of formula (I) are of formula (Ia):

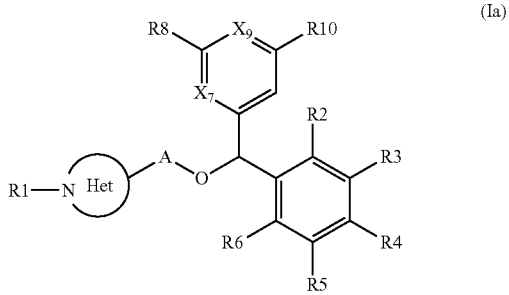

(Ia)

wherein
R1, Het, A, R2-6 are defined as in claim 1
X7 or X9 represents —N= and the other of X7 or X9 represents —CR7= or —CR9=
And where R8, R10 and optional R7 or R9, identical or different are chosen from
H and Ri' wherein Ri' is selected from
halo, cyano,
alkyl; optionally substituted with one or more of halo;
aryl; wherein at least one of R7, R8, R9 and R10 is chosen from Ri';
and wherein R9 and R10 can form together with the C atoms to which they are attached an aromatic ring
as well as their enantiomers, diastereomers, mixtures thereof and pharmaceutically acceptable salts, tautomers, hydrates and solvates.

3. Compounds according to claim 1, wherein the compounds of formula (I) are of formula (Ib):

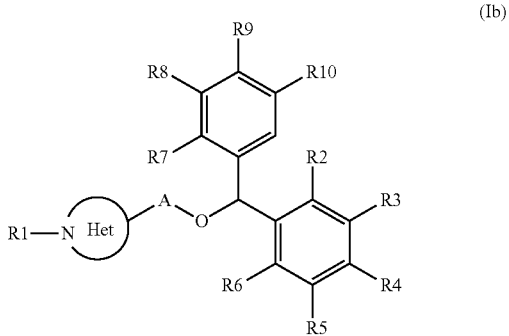

(Ib)

wherein:
R1, Het, A, R2-6 are defined as in claim 1 and
each of R7-R10 is chosen from
H and Ri', wherein Ri' is chosen from:
halo, cyano,
alkyl; optionally substituted with halo;
aryl;
and wherein R9 and R10 can form together with the C atoms to which they are attached an aromatic ring; and
wherein at least one of R7-R10 is chosen from Ri',
as well as their enantiomers, diastereomers, mixtures thereof and pharmaceutically acceptable salts, tautomers, hydrates and solvates.

4. Compounds according to claim 1, wherein R1 represents a methyl.

5. Compounds according to claim 1 selected from the group consisting of:
2-[(2-Fluoro-5-trifluoromethoxyphenyl)(1-methylpiperidin-4-yloxy)methyl]pyridine
5-Chloro-2-[(2-fluoro-4-methylphenyl)(1-methylpiperidin-4-yloxy)methyl]pyridine
2-[(2-Fluoro-4-methylphenyl)(1-methylpiperidin-4-yloxy)methyl]pyridine
5-Chloro-2-[(2-fluoro-5-trifluoromethoxyphenyl)(1-methylpiperidin-4-yloxy)methyl]pyridine
6-{3-[(1-Methylpiperidin-4-yloxy)pyridin-2-ylmethyl]phenyl}hex-5-ynylamine
4-[(2-Fluoro-5-trifluoromethoxyphenyl)(1-methylpiperidin-4-yloxy)methyl]pyridine
2-[(2-Fluoro-4-methylphenyl)(1-methylpiperidin-4-yloxy)methyl]-4-methylpyridine
2-[(2-Fluoro-5-trifluoromethoxyphenyl)(1-methylpiperidin-4-yloxy)methyl]-4-methylpyridine
5-Chloro-2-[(4-chlorophenyl)(1-methylpiperidin-4-yloxy)methyl]pyridine
5-Fluoro-2-[(2-fluoro-4-methylphenyl)(1-methylpiperidin-4-yloxy)methyl]pyridine
5-Fluoro-2-[(2-fluoro-5-trifluoromethoxyphenyl)(1-methylpiperidin-4-yloxy)methyl]pyridine
5-Chloro-2-[(3-methoxyphenyl)(1-methylpiperidin-4-yloxy)methyl]pyridine
5-Chloro-2-[(3-iodophenyl)(1-methylpiperidin-4-yloxy)methyl]pyridine
2-[(2-Fluoro-4-methylphenyl)(1-methylpiperidin-4-yloxy)methyl]-4-trifluoromethylpyridine
2,3-Difluoro-6-[(5-fluoropyridin-2-yl)(1-methylpiperidin-4-yloxy)methyl]phenol
6-[(5-Chloropyridin-2-yl)(1-methylpiperidin-4-yloxy)methyl]-2,3-difluorophenol
(6-{3-[(1-Methylpiperidin-4-yloxy)pyridin-2-ylmethyl]phenyl}hex-5-ynyl)carbamic acid ethyl ester
6-{3-[(5-Chloropyridin-2-yl)(1-methylpiperidin-4-yloxy)methyl]phenyl}hex-5-ynylamine
2-[(1-Methylpiperidin-4-yloxy)pyridin-2-ylmethyl]phenol
5-Fluoro-2-[(5-fluoropyridin-2-yl)(1-methylpiperidin-4-yloxy)methyl]phenol
2-Fluoro-6-[(5-fluoropyridin-2-yl)(1-methylpiperidin-4-yloxy)methyl]-3-methylphenol
6-[(5-Chloropyridin-2-yl)(1-methylpiperidin-4-yloxy)methyl]-2-fluoro-3-methylphenol
2-[(5-Chloropyridin-2-yl)(1-methylpiperidin-4-yloxy)methyl]-5-fluorophenol
2-[(5-Fluoropyridin-2-yl)(1-methylpiperidin-4-yloxy)methyl]-5-methylphenol
2-[(5-Chloropyridin-2-yl)(1-methylpiperidin-4-yloxy)methyl]-5-methylphenol
2-Fluoro-6-[(4-fluoropyridin-2-yl)(1-methylpiperidin-4-yloxy)methyl]-3-methylphenol
4-[(3-Iodophenyl)-p-tolylmethoxy]-1-methylpiperidine
4-[(2-Fluoro-5-trifluoromethoxyphenyl)naphthalen-2-yl-methoxy]-1-methylpiperidine
4-[(2-Fluoro-4-methylphenyl)naphthalen-2-yl-methoxy]-1-methylpiperidine 4-[(3,4-Dichlorophenyl)(2-fluoro-4-methylphenyl)methoxy]-1-methylpiperidine 4-[(3,4-Dichlorophenyl)(2-fluoro-5-trifluoromethoxyphenyl)methoxy]-1-methylpiperidine 4-[(2-Fluorophenyl)-(2-fluoro-5-trifluoromethoxyphenyl)methoxy]-1-methylpiperidine 4-[(4-Chlorophenyl)(2-fluoro-5-trifluoromethoxyphenyl)methoxy]-1-methylpiperidine 4-[(4-Chlorophenyl)(2-fluoro-4-methylphenyl)methoxy]-1-methylpiperidine 4-[(4-Chlorophenyl)(3-iodophenyemethoxy]-1-methylpiperidine 6-{3-[(4-Chlorophenyl)(1-methylpiperidin-4-yloxy)methyl]phenyl}hex-5-ynylamine; and 2-[(3-Iodophenyl)(1-methylpiperidin-4-yloxy)methyl]pyridine as well as their enantiomers, diastereomers, mixtures thereof and pharmaceutically acceptable salts, tautomers, hydrates and solvates.

6. Process of preparation of the compounds of formula (I) according to claim 1 comprising condensing an alcohol of formula (III) in which R1, Het and A are as defined in claim 1 with an alcohol of formula (IV) in which R2, R3, R4, R5, R6, X7, X8, X9 and X10 are as defined in claim 1:

7. Process of preparation of the compounds of formula (I) according to claim 1 comprising condensing an alcohol of formula (III) in which R1, Het and A are as defined in claim 1 with an alkylating agent of formula (V) in which R2, R3, R4, R5, R6, X7, X8, X9 and X10 are as defined in claim 1 and X represents a halogen or a leaving group such as a mesylate, a triflate, a nosylate or a tosylate

8. Process of preparation of the compounds of formula (I) according to claim 1 comprising functionally modifying a corresponding compound of formula (I) as defined in claim 1.

9. The process according to claim 6 further comprising the additional step of isolating the desired compound.

10. A pharmaceutical composition comprising a compound of formula (I) according to claim 1 with a pharmaceutically acceptable excipient.

11. A combination of a compound according to claim 1 with one or more therapeutic agent(s) selected from the group consisting of:

Histamine $H_1$, $H_2$ or $H_3$ receptor antagonists,

Leukotriene antagonists,

5-Lipoxygenase (5-LO) inhibitors or 5-lipoxygenase activating protein (FLAP) antagonists, $CX_1$- and $\alpha_2$-adrenoceptor agonist vasoconstrictor sympathomimetic agents for decongestant use, Xanthines, Steroidal and non-steroidal antiinflammatories, Ketotifen, COX-1 inhibitors (NSAIDs) and COX-2 selective inhibitors, Immunosuppressants, and mucolytics or anti-tussive agents.

12. The combination according to claim 11, wherein the H1R antagonist is selected from the group consisting of cetirizine, desloratadine, bepotastine and doxepin.

13. The combination according to claim 11, wherein the Xanthines, are selected from the group consisting of theophylline and aminophylline.

14. The combination according to claim 11, wherein the steroidal and non-steroidal anti-inflammatories are selected from the group consisting of sodium cromoglycate and nedocromil sodium.

* * * * *